United States Patent [19]
Brennan et al.

[11] 3,943,162
[45] Mar. 9, 1976

[54] CYANOETHYLATION OF AROMATIC AMINES
[75] Inventors: Michael E. Brennan; Ernest Leon Yeakey, both of Austin, Tex.
[73] Assignee: Jefferson Chemical Co., Inc., Houston, Tex.
[22] Filed: Apr. 16, 1975
[21] Appl. No.: 568,794

[52] U.S. Cl. .................................. 260/465 E
[51] Int. Cl.² ................................. C07C 121/78
[58] Field of Search ......................... 260/465 E

[56] References Cited
UNITED STATES PATENTS
3,496,213  2/1970  Ross ............................ 260/465

Primary Examiner—Lewis Gotts
Assistant Examiner—Dolph A. Torrence
Attorney, Agent, or Firm—James L. Bailey; John R. Kirk, Jr.; Lee G. Meyer

[57] ABSTRACT

An improved process is disclosed for the production of cyanoethylated aromatic amines comprising contacting an aromatic amine with acrylonitrile in the presence of a silica–alumina catalyst in a liquid phase reaction at elevated temperature. Aromatic polyamines are cyanoethylated according to the process of this invention to form a reaction product comprising poly-(N-monocyanoethylated) aromatic amines and poly-(N-monocyanoethylated) aromatic amines additionally having at least one cyanoethyl group attached to the nucleus of the aromatic ring.

10 Claims, No Drawings

CYANOETHYLATION OF AROMATIC AMINES

BACKGROUND OF THE INVENTION

1. Field of the Invention

This invention relates to cyanoethylated derivatives of aromatic amines and to an improved process for the production of such compounds. In particular, this invention relates to an improved process for cyanoethylation of aromatic amines wherein N-monocyanoethylated aromatic amines are the predominant product. Such cyanoethylated aromatic amines are of established utility as polyurethane chain extenders, and as intermediates in the production of bactericidal substances, antioxidants and dyestuffs. The cyanoethylated aromatic amines may be hydrogenated to the corresponding 3-aminopropyl primary amine derivatives which are useful as epoxy curing agents.

2. Prior Art

Although aliphatic amines can be reacted with acrylonitrile to form the corresponding cyanoethyl amine derivative in uncatalyzed reactions, aromatic amines do not react with acrylonitrile in the absence of a catalyst. Cyanoethylation is known to proceed with aromatic amines in the presence of acidic catalyst, e.g. acetic acid, cuprous chloride, cuprous acetate and mineral acids. See for example U.S. Pat. No. 2,726,945 and U.S. Pat. No. 3,231,601. All of these catalysts are homogeneous catalysts and are unsatisfactory in that they present problems in the recovery of the desired product from the crude reaction mixture.

SUMMARY OF THE INVENTION

Now, according to the instant invention, a process is disclosed for the production of cyanoethylated derivatives of aromatic amines which comprises contacting an aromatic amine with acrylonitrile in the presence of a silica-alumina catalyst at a temperature of from about 80°C to about 300°C. Aromatic monoamines are cyanoethylated to the N-monocyanoethyl derivative in high yield. Aromatic polyamines, such as aromatic diamines and polymethylene polyphenylene polyamines are cyanoethylated to reaction products comprising poly-(N-monocyanoethylated) aromatic polyamines and poly-(N-monocyanoethylated) aromatic polyamines additionally having at least one cyanoethyl group attached to the nucleus of the aromatic ring.

DESCRIPTION OF THE PREFERRED EMBODIMENTS

According to the instant process, acrylonitrile reacts with one of the active hydrogen atoms of the aromatic amine at an elevated temperature in the presence of the catalyst as herein described to form the mono-cyanoethyl derivative of the aromatic amine. After the addition of one cyanoethyl group to the amine nitrogen, the second amine hydrogen atom does not readily undergo further reaction with acrylonitrile. Thus, with aromatic monoamines there is but one cyanoethylated derivative in the reaction product.

Aromatic polyamines react with acrylonitrile according to the process of this invention to form a reaction product comprising a mixture of cyanoethylated derivatives. The reaction products are characterized in the following equation in which ortho-phenylenediamine is selected as exemplary of an aromatic diamine.

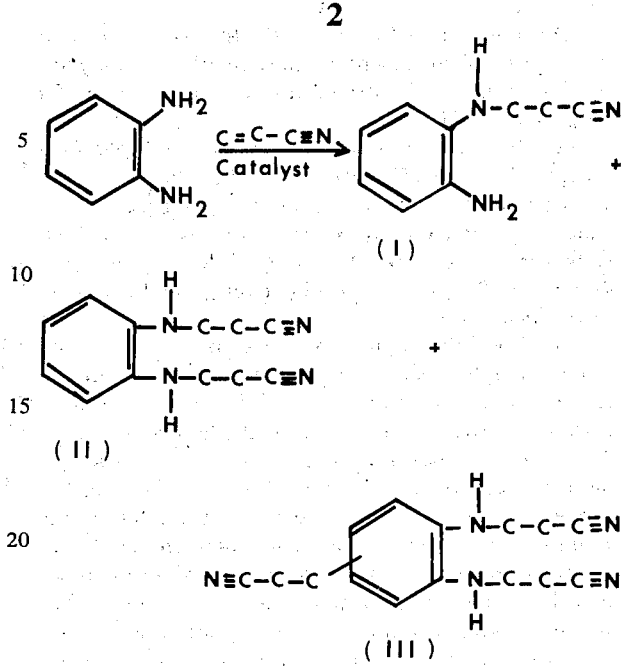

From the preceeding equation it can be seen that the reaction product comprises a mixture of mono-N-cyanoethylated aromatic diamine, di-N-monocyanoethylated aromatic diamine and a tricyanoethylated aromatic amine in which the third cyanoethyl group is attached directly to the nucleus of the aromatic ring. One of the advantages of the process of this invention is the formation of the ring-substituted cyanoethyl derivatives of aromatic polyamines, such as those represented by formula III above. Another advantage of the process of this invention is that the reaction of acrylonitrile with the hydrogen of the amine group of the aromatic amine results primarily in N-monocyanoethyl derivatives. Only with an aromatic diamine, in which the amine groups are in the para position relative to one another, does cyanoethylation of both amine hydrogens occur to any substantial extent.

The aromatic amines which may be employed in practicing the process of this invention, are primary amines and include aromatic monoamines, aromatic diamines and polymethylene polyphenylene polyamines such as those described in U.S. Pat. No. 3,362,979. Of course, such aromatic amines may contain substituent groups which are of a non-interfering nature such as alkyl, alkoxy, hydroxy and the like. Illustrative aromatic amines include the aromatic monoamines such as aniline, the toluidines and the like; the aromatic diamines such as the phenylene diamines (o-, m- and p-isomers), toluenediamine (2,4- and 2,6-isomers), methylene dianiline (all isomers) and the like; and the polymethylene polyphenylene polyamines having a functionality of from about 2.1 to about 3.0. Such polymethylene polyphenylene polyamines which are suitable in the practice of this invention, are more fully described in U.S. Pat. No. 3,362,979, which is herein incorporated by reference.

The catalysts which are useful in practicing the process of this invention are generally referred to as silica-aluminas. The silica-aluminas which are effective as catalysts include those having an alumina content of from about 5 to about 50 wt. %, and preferably from about 10 to about 40 wt. %. The silica-aluminas, as herein described, catalyze the cyanoethylation of aromatic amines to produce the cyanoethylated derivatives in good yields and with high selectivity. While most any silica-alumina with an alumina content within the above-mentioned range is effective as a catalyst in the process of this invention, particularly desirably are silica-aluminas with surface areas of from about 50 m²/g to about 700 m²/g.

The silica-alumina catalysts can be employed in a fine powder or in a pelletized form. Pelletized catalysts are particularly suitable for continuous processes in which the catalyst may be employed as a fixed bed. However, the form in which the catalyst is employed, seemingly does not alter its effectiveness in the process of this invention.

From the above equations it can be seen that one mole of acrylonitrile will react with each mole equivalent of amino function to form the N-monocyanoethylated derivative of the aromatic amine reactant. Therefore, whenever aromatic monoamines such as aniline or the toluidines are employed in practicing the process of this invention, one mole of acrylonitrile is required for each mole of aromatic monoamine. Whenever aromatic diamines such as the phenylene diamines and the like are employed in practicing the process of this invention, two moles of the acrylonitrile reactant per mole of amine reactant are required. However, acrylonitrile is generally supplied in excess of the stoichiometric ratio in order to ensure a high conversion level of the aromatic amine. Also, whenever aromatic polyamines are employed as the reactant, additional acrylonitrile is required in excess of the stoichiometric amount to provide the acrylonitrile necessary for the substantial proportion of ring-cyanoethylated product (formula III above) that is produced. Generally, acrylonitrile is employed in an amount to provide from about 10% to about 100% in excess of the stoichiometric amount as herein described. Of course, greater amounts may be employed if desired in order to ensure the desired degree of cyanoethylation.

The cyanoethylation reaction of this invention is carried out in a liquid phase reaction which is conducted at a temperature of from about 80°C to about 300°C, and preferably at a temperature of from about 100°C to about 175°C. Of course, the temperature selected will depend upon the particular reactants employed and the desired conversion levels.

The pressure at which the reaction is carried out can be at any pressure sufficient to maintain the reactants and products substantially in the liquid state. Generally, reaction pressures of from about atmospheric to about 500 psig are satisfactory with pressures of from about 25 psig to about 100 psig being preferred. Of course, higher reaction zone pressures may be employed, if desired.

The amount of catalyst employed in the process of this invention will depend, of course, on the type of catalyst and the particular aromatic amine which is to be cyanoethylated. In batch processes, a silica-alumina catalyst, employed in an amount of from about 1 to about 20 wt. %, based upon the amount of aromatic amine reactant present, has been found satisfactory, with an amount of from about 5 to about 15 wt. %, upon the same basis, being preferred.

The aromatic amine and acrylonitrile mixture is maintained in contact with the catalyst under reaction conditions for a period of time necessary to obtain the desired degree of conversion to products. Generally, a reaction period of from about 1 to about 10 hours will be sufficient. In a continuous reaction process wherein the catalyst is generally employed as a fixed bed, a weight hourly space velocity (WHSV) of from about 0.1 to about 5.0 g/ml catalyst/hr is satisfactory with a space velocity of from about 0.2 to about 2.0 g/ml catalyst/hr being preferred.

In practicing the process of this invention, a solvent is not required but may be employed if desired. Whenever a solvent is employed, the solvent should be inert to the reaction environment and not interfere with the desired reaction. Acetonitrile is an example of a suitable solvent which may be employed in practicing the process of this invention. Whenever a solvent is employed, the amount used is not critical and will generally be in the range of from about 10% to about 100% by weight based on the reactants.

The crude reaction product obtained from the process of this invention will comprise the desired N-monocyanoethylated aromatic amine product in combination with the partially N-cyanoethylated derivatives as herein described, unreacted aromatic amine, and unreacted acrylonitrile. In some emobdiments of the process of this invention, the catalyst will also be present in the crude reaction mixture, for example, in batch processes and in continuous processes where the heterogeneous catalyst is employed in intimate admixture with the reactants. The catalyst is present in the reaction product and may be recovered from the crude reaction mixture and recycled for reuse according to the process of this invention. It is generally preferable to wash the recovered catalyst, for example with methanol and/or water and dry it prior to recycling it for reuse.

The N-monocyanoethylated aromatic amines are recovered from the crude reaction mixture by conventional means, for example distillation, extraction and the like. Similarly, the unreacted acrylonitrile and aromatic amine may be recovered and recycled for conversion to the desired product according to the process of this invention. Likewise, the partially N-monocyanoethylated aromatic polyamine may be recovered and recycled for further cyanoethylation as herein described.

The N-cyanoethylated aromatic amines of this invention are useful as chain extenders in polyurethane compositions and are particularly suitable as a replacement for MOCA (3,3'-dichloro-4,4'-diaminodiphenylmethane) as an ingredient in molding elastomer formulations.

The process of this invention will now be further illustrated in the following examples which are for the purposes of illustration and should not be considered a limitation on the scope of the invention.

EXAMPLES 1-6

In each of the following runs, a dry, nitrogen-purged, stirred autoclave was charged with an aromatic amine, acrylonitrile and silica-alumina catalyst. Then a nitrogen atmosphere was established in the autoclave and the autoclave contents were heated to a temperature and held at a certain pressure for the time indicated in the following Table 1.

TABLE 1

| Run[1] No. | Amine | g AN / 100 g amine | Catalyst wt. % | Temp., °C. | Reaction time hours | Pressure psig | Product Isolated wt., g | % N | Total amine, meq/g. | NMR, | moles AN added[12] / mole amine |
|---|---|---|---|---|---|---|---|---|---|---|---|
| 1 | JEFFAMINE AP-20[2] 198.3 g (1.0 mole) | 61.6 | 7.5 | 146–152 | 6.0 | 70–45 | 287.7 | — | 6.25[6] | | 1.60 |
| 2 | JEFFAMINE AP-20 1586.0 g (8.0 mole) | 64.2 | 10.0 | 158–162 | 6.0 | 78–34 | 2336.6[7] | 17.57[8] | 6.09[6] | | 1.95 |
| 3 | JEFFAMINE AP-22[3] 1586.0 g | 62.2 | 10.0 | 158–161 | 6.0 | 82–41 | 2241.0 | 17.39 | 6.30[9] | | 1.60 |
| 4 | JEFFAMINE AP-27[4] 1586.0 g | 61.6 | 10.0 | 158–161 | 6.0 | 82–47 | 2267.0 | 17.30 | 6.22[10] | | 1.60 |
| 5 | JEFFAMINE AP-22 21.0 lbs. | 54.3 | 20.0 | 125 | 9.0 | 37–14 | — | 17.74 | 6.60 | | 1.70–1.80 |
| 6 | 4,4'-MDA 99.1 g (0.5 mole) | 214.0[5] | 10.0 | 155–161 | 6.0 | 95–88 | 133.0[11] | 17.40[8] | 7.30[6] | | 1.50 |

ANNEX TO TABLE 1

[1] Runs No. 1 and No. 6 were carried out in a one-liter stirred autoclave; Runs 2–4 were carried out in a 1 gallon autoclave, and Run 5 was carried out in a 5 gallon kettle.

[2] 97.9 wt.% isomeric methylenedianiline (5.6%, 2,2' isomer, 25.3%, 2,4' isomer, 69.0%, 4,4' isomer-MDA); total amine 10.08 meq/g.

[3] A mixture of methylene dianiline isomers and polymethylene polyphenylene polyamine having an average functionality of 2.2 (60.7 wt.% isomeric MDA; total amine 9.76 meq/g.)

[4] A mixture of methylene dianiline isomers and polymethylene polyphenylene polyamine having an average functionality of 2.7 (48.6 wt.% isomeric MDA; total amine 9.67 meq/g.)

[5] 200 ml of acetonitrile used as solvent

[6] Theor. 6.57 meq/g.

[7] 96.0% of theory

[8] Theor. 18.41%

[9] Theor. 6.43 meq/g.

[10] Theor. 6.39 meq/g.

[11] Tertiary amine: 0.01 meq/g.; total acetylatables: 7.11 meq/g.

[12] In Runs 1 through 5 approximately 10–15% of the cyanoethylation occurred as ring-cyanoethylation. In Run 6 the extent of ring-cyanoethylation was approximately 20% (1.20-NHCH$_2$CH$_2$CN and 0.30 nuclear (one ring) cyanoethylation.)

Thereafter, the autoclave was cooled and the reaction mixture was filtered through filter aid to remove the catalyst. Small amounts of acetonitrile were used to wash the filter aid and catalyst to recover all of the product. The resulting filtrate was stripped of volatiles at aspirator pressure by means of a rotary evaporator and the resulting liquid product was analyzed by infrared (IR) and nuclear magnetic resonance (NMR) spectroscopy in order to characterize the products.

An examination of the data in Table 1 shows that the silica-alumina is an effective catalyst in cyanoethylating the aromatic polyamines. In Example No. 6, where a large excess of acrylonitrile was employed, a larger proportion of product was characterized as having nuclear (ring) cyanoethylation.

EXAMPLES 7–25

According to the general procedure of Examples 1–6, the effectiveness of a silica-alumina catalyst for cyanoethylating various other aromatic amines and aromatic polyamines was investigated. The data presented in the following Table 2 show that a silica-alumina catalyst was effective in cyanoethylating aniline, ortho-phenylenediamine (o-PDA), meta-phenylenediamine (m-PDA), para-phenylenediamine (p-PDA), toluenediamine (TDA) and toluidine (all isomers). While the catalyst promoted cyanoethylation of both aromatic monoamines and aromatic polyamines, ring cyanoethylation occurred only with the aromatic polyamines. The data also show that attempts to cyanoethylate aromatic compounds not having an amine group were unsuccessful.

TABLE 2

| Run[1] No. | substrate (moles) | Acrylonitrile (moles) | Acetonitrile solvent (ml) | Temp., °C. | Press., psig |
|---|---|---|---|---|---|
| 7 | o-PDA (1.0) | 2.4 | 100 | 159–161 | 84–78 |
| 8 | o-PDA (1.0) | 4.0 | 200 | 160–162 | 88–84 |
| 9 | m-PDA (1.0) | 2.4 | 100 | 155–161 | 83–75 |
| 10 | m-PDA (1.0) | 4.0 | 200 | 159–162 | 92–85 |
| 11 | p-PDA (1.0) | 2.4 | 300 | 160–164 | 93–84 |
| 12 | p-PDA (1.0) | 4.0 | 200 | 160–165 | 96–85 |
| 13 | 2,4-TDA (1.0) | 2.4 | 100 | 160–165 | 89–77 |
| 14 | 2,4-TDA (1.0) | 4.0 | 200 | 158–162 | 90–84 |
| 15 | Aniline (1.8) | 3.6 | — | 161–163 | 70–65 |
| 16 | Aniline (10.0) | 12.0 | — | 164–158 | 75–43 |
| 17 | o-Toluidine (0.89) | 3.6 | — | 158–165 | 92–80 |
| 18 | m-Toluidine (0.89) | 3.6 | — | 155–165 | 88–81 |

TABLE 2-continued

| Run[1] No. | substrate (moles) | Acrylonitrile (moles) | Acetonitrile solvent (ml) | Temp., °C. | Press., psig |
|---|---|---|---|---|---|
| 19 | p-Toluidine (0.89) | 3.6 | — | 160–162 | 88–83 |
| 20 | Benzene (2.0) | 4.4 | — | 157–164 | 117–102 |
| 21 | Benzene (2.0) | 4.4 | — | 177–183 | 172–158 |
| 22 | Toluene (2.0) | 4.0 | — | 179–182 | 140–132 |
| 23 | Toluene (2.0) | 4.0 | — | 198–202 | 200–190 |
| 24 | Nitrobenzene (1.5) | 3.0 | — | 180–182 | 112–108 |
| 25 | Phenol (1.0) | 4.0 | — | 159–162 | 84–78 |

| | | | Product | | | |
|---|---|---|---|---|---|---|
| Isolated wt., g | Total amine meq/g | Total acet., meq/g | Tertiary amine meq/g | Prim. amine meq/g | % N | % Ring $-CH_2CH_2CN$ (NMR) | % Cyanoethylation of amino Group (s) |
| 120.0 | | | | | | — | 50.0 |
| 163.0 | | | | | | 20–25 | 50.0 |
| 190.0 | | | | | | 35 | — |
| 177.0 | | | | | | 35 | 50.0 |
| 208.0[2] | | | | | | | 100.0 |
| 35.0 | | | | | | 0[5] | 75.0 |
| 151.0 | | | | | | 100 | 100.0 |
| 198.0 | | | | | | 35 | 50.0 |
| 167.0 | | | | | | 25 | 45.0 |
| 273.0 | 6.78[3] | 6.58[3] | — | — | — | 0[6] | 100.0 |
| 1370.7 | 7.14[3] | 7.58[3] | 0.01 | — | 17.7[4] | 0[7] | 83.0 |
| 122.0 | 7.10 | 6.97 | — | — | — | 0[8] | 50.0 |
| 140.0 | 6.15 | 5.89 | — | — | — | 0[9] | 100.0 |
| 150.8 | 5.95 | 6.78 | — | — | — | 0[10] | 100.0 |
| — | — | NO REACTION | | — | — | — | — |
| — | — | " | | — | — | — | — |
| — | — | " | | — | — | — | — |
| — | — | " | | — | — | — | — |
| — | — | " | | — | — | — | — |

ANNEX TO TABLE 2
[1]Run No. 16 was run in a 1 gallon autoclave; all other runs were carried out in a 1 liter autoclave.
[2]m.p. 139–140°C.
[3]Theor. 6.85 meq/g.
[4]Theor. 19.15%
[5]Product characterized as p-PDA; tris-NH addition
[6]Product characterized as $C_6H_5NHCH_2CH_2CN$
[7]83% conv.; 93.5% yield
[8]50% conversion
[9]100% conversion
[10]100% conversion While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. In a process for cyanoethylation of aromatic amines selected from the group of aromatic monoamines, aromatic diamines and polymethylene polyphenyl polyamines having an average functionality of from about 2.0 to about 3.0, with acrylonitrile, the improvement which consists essentially of contacting the reactants at a temperature of from about 80°C to about 300°C in the liquid phase in the presence of a silica-alumina catalyst having an alumina content of from about 5 to about 50 weight percent, the catalyst being present in an amount of from about 1 to about 20 percent by weight, based upon the aromatic amine, and recovering cyanoethylated aromatic amines from the reaction mixture.

2. The process according to claim 1 wherein the silica-alumina catalyst has an alumina content of from about 10 to about 40 weight percent and has a surface area of from about 50 to about 700 m²/g.

3. The process according to claim 2 wherein the silica-alumina catalyst is present in an amount of from about 5 to about 15 percent by weight, based upon the aromatic amine reactant.

4. The process according to claim 3 wherein the contacting is carried out at a temperature of from about 100°C to about 175°C.

5. The process according to claim 4 wherein acrylonitrile is present in an amount such that the mole ratio of acrylonitrile to amine group is from about 1.10 to about 2.0.

6. The process according to claim 5 wherein the aromatic amine is an aromatic monoamine selected from the group of aniline and the toluidines, and the N-(monocyanoethyl) aromatic amine derivative is recovered from the reaction mixture.

7. The process according to claim 5 wherein the aromatic amine is an aromatic diamine selected from the group of the methylenedianilines, the phenylenediamines and the toluenediamines.

8. The process according to claim 5 wherein the aromatic amine is a polymethylene polyphenylene polyamine having an average functionality of from about 2.0 to about 3.0.

9. The process according to claim 7 wherein the aromatic amine is methylene dianiline (4,4'—, 2,4'—, or 2,2'—) or its isomeric mixtures.

10. The process according to claim 1 wherein the silica-alumina catalyst is recovered from the reaction mixture and is recycled for reuse.

\* \* \* \* \*